Figure 1:
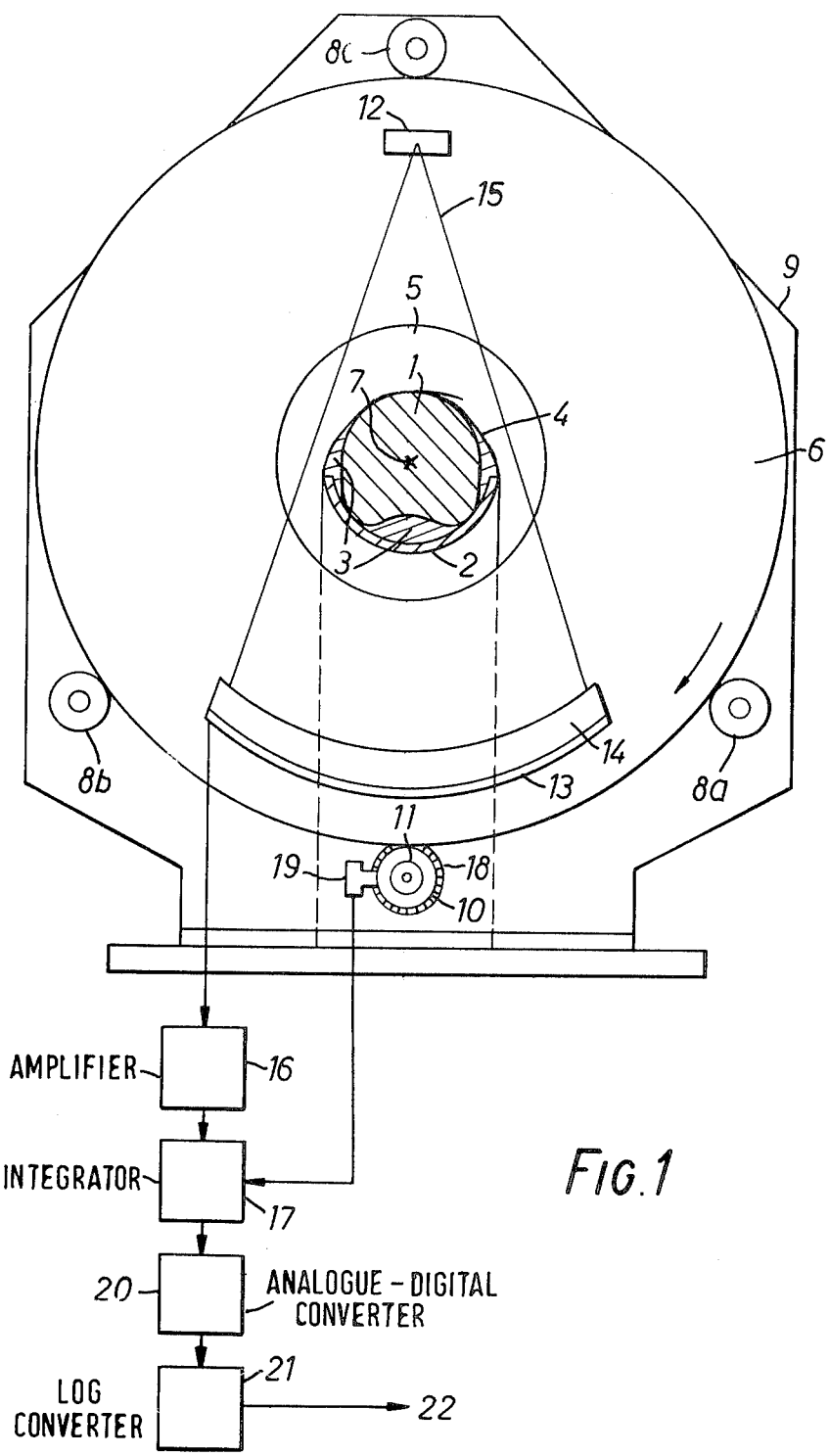

United States Patent [19]

Logan et al.

[11] 4,091,286
[45] May 23, 1978

[54] RADIOGRAPHY APPARATUS WHEREIN INTERLEAVING OF BEAM PATHS IS EFFECTED BY CHANGING THE PHASE OF THE TIMING PULSES

[75] Inventors: Allan Beattie Logan, London; Robin Geoffrey Marsh, Reading; Ian Alexander Fleming, Maidenhead, all of England

[73] Assignee: EMI Limited, Hayes, England

[21] Appl. No.: 764,018

[22] Filed: Jan. 31, 1977

[30] Foreign Application Priority Data
Feb. 10, 1976 United Kingdom ................. 5138/76

[51] Int. Cl.² ...................... A61B 6/02; G01N 23/08; H05G 1/30
[52] U.S. Cl. ................................ 250/360; 250/445 T
[58] Field of Search ........................... 250/445 T, 360

[56] References Cited
U.S. PATENT DOCUMENTS 3,934,142  1/1976  Hounsfield ........................ 250/360
4,044,260  8/1977  Hounsfield ........................ 250/360

Primary Examiner—Alfred E. Smith
Assistant Examiner—T. N. Grigsby
Attorney, Agent, or Firm—Cooper, Dunham, Clark, Griffin & Moran

[57] ABSTRACT

In computerized tomographic apparatus in which radiation from a source is projected through a body along a plurality of substantially linear beam paths and the source is rotated around the body, interleaving of beam paths is effected by changing the phase of timing pulses, with respect to the rotational movement, at a suitable stage in the scan. A bank of detectors is used to detect the radiation emergent from the body along said paths and a feature of the invention is to change the phase for each detector at a respective time so that no beam paths are duplicated but all sets of interleaved and original beam paths are completed in a single revolution of the scan.

9 Claims, 2 Drawing Figures

TABLE 1.

RADIOGRAPHY APPARATUS WHEREIN INTERLEAVING OF BEAM PATHS IS EFFECTED BY CHANGING THE PHASE OF THE TIMING PULSES

The present invention relates to radiography and, in particular, to that branch of radiography which has become known as computerised axial tomography (C.A.T.). By means of C.A.T., it is possible to evaluate the absorption coefficient, with respect to penetrating radiation, such as X-radiation, at each of a plurality of elemental locations distributed over a cross-sectional slice of a body under examination. It is usual to provide a visual display of the evaluated coefficients.

In order to permit the aforementioned coefficients to be evaluated, it is necessary to obtain signals indicative of the absorption suffered by the radiation on traversing each of a large number of beam paths through the body in the slice. It is usual to obtain these signals by causing a source of the radiation to project radiation through the body along one or more of said paths towards detector means positioned to receive the radiation emergent from the body along the path or paths and scanning the source and the detector means relative to the body to cause the remainder of said beam paths to be irradiated and to produce the required signals. These signals are then processed in any convenient manner, such as that disclosed in U.S. Pat. No. 3,778,614 or that disclosed in U.S. Pat. No. 3,924,129 to evaluate said coefficients.

The rapid acquisition of the signals concerned is clearly desirable, since the faster the signals can be acquired, the lower is the chance of the body, or of an organ or fluid within it, moving and causing errors in the evaluation of said coefficients. To this end, it has been proposed to use a source of a substantially planar, fan-shaped spread of the radiation, the spread being disposed in the said slice, and a plurality of detector devices distributed across the spread of radiation so that a group of many (e.g. 100 or more) of the paths can be irradiated at one and the same time and the corresponding output signals derived. Provided that the spread is sufficiently broad to encompass at least a substantial part of the body, all of the desired signals can be obtained, group by group, by rotating the source and the detector devices around the body about a common axis which intersects the said slice.

The output signals derived from any one detector are rendered distinguishable from one another by means of sampling pulses, relating to the progress of the rotational movement; many such pulses being developed during the rotation of said source and said detector means about the body.

It is an object of this invention to increase the number of groups of output signals which can be derived from an apparatus of the kind described above without the necessity for additional source or detector components.

According to the invention there is provided radiographic apparatus comprising a source of a substantially planar spread of penetrating radiation, means for supporting said source to project said radiation across an opening in which a body to be examined can be inserted, the spread of radiation being disposed to irradiate a selected cross-sectional slice of said body, means for angularly moving said means for supporting, and with it said source, about an axis intersecting said slice, a plurality of detector devices disposed to receive radiation directed through said slice along a plurality of groups of divergent beam paths, in said slice, during said angular movement, a signal channel for each detector device arranged to receive output signals, developed by said detector devices and indicative of the absorption suffered by said radiation on traversing said beam paths, and means for generating timing signals for application to said channels to distinguish the output signals relating to each of said groups, said timing signals being related to the angular movement of said means for supporting relative to said body, and means, effective during said angular movement for changing the relationship between said timing signals and said angular movement, so as to derive output signals relating to more of said groups of beam paths than would have been available without said change of relationship.

Figure 2:
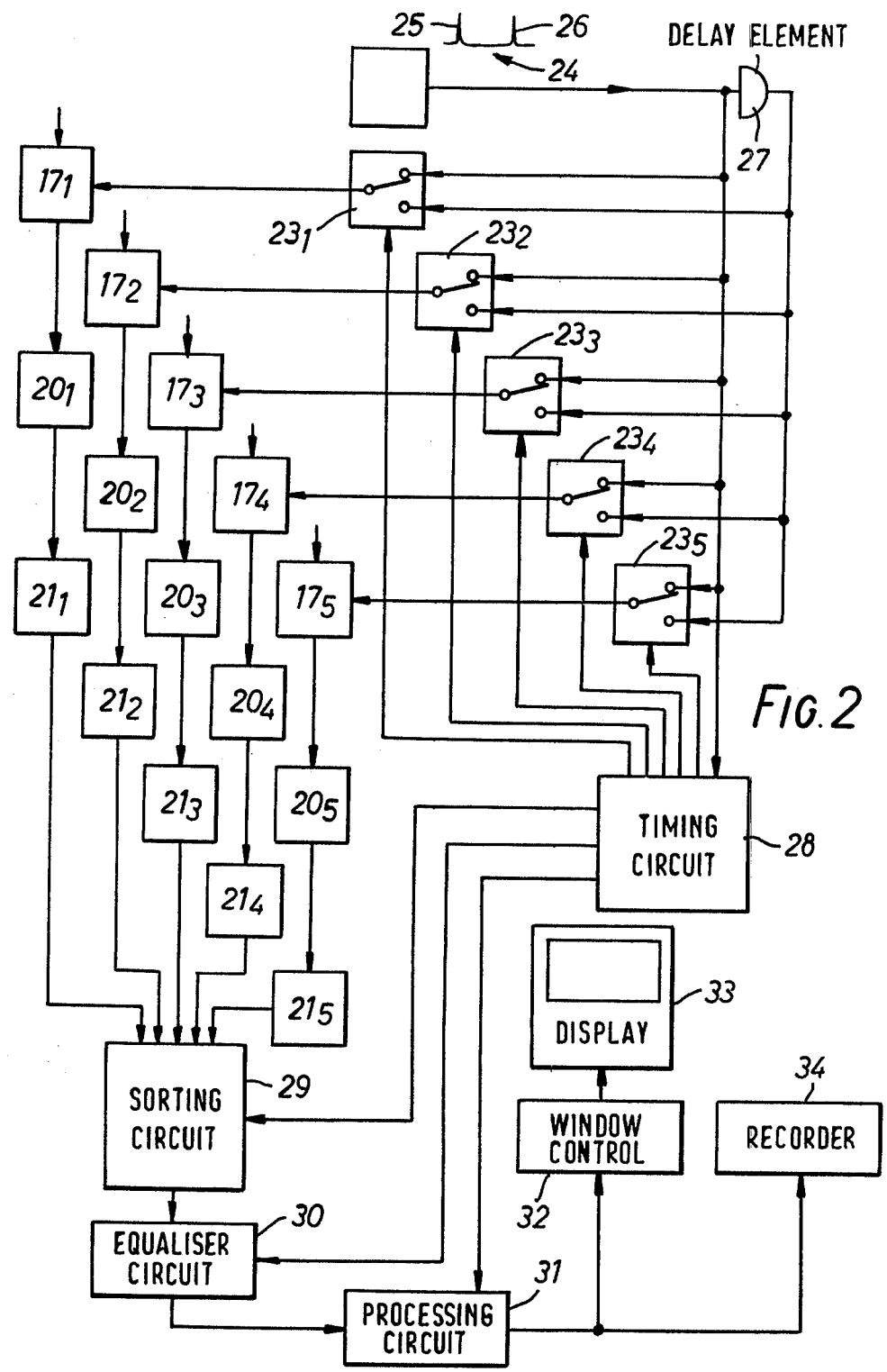

It has previously been proposed, for example in U.S. application Ser. No. 489,084 now U.S. Pat. No. 3,934,142 to increase the number of groups of beam paths irradiated by physically shifting the detectors relative to the source, either abruptly at an appropriate stage in the rotational scanning movement or progressively throughout the rotational scanning movement. The present invention permits such a physical shift to be dispensed with, whilst retaining the advantageous increase in the number of groups of beam paths irradiated. In order that the invention may be clearly described and readily carried into effect, one embodiment thereof will now be described, by way of example onlly, with reference to the accompanying drawings of which:

FIG. 1 shows, in front elevation, part of an apparatus suitable for use in accordance with one example of the invention, and FIG. 2 shows, in block schematic form, part of a circuit arrangement for causing said apparatus to operate in accordance with said example of the invention.

Referring now to FIG. 1, a body 1, of a patient to be examined, is shown in transverse section supported on a suitably shaped bed 2, also shown in transverse section. A material 3, having an absorption to the radiation similar to that of body tissue, is positioned between the body 1 and bed 2, partly to support the patient and partly to exclude air from the gap therebetween, and is extended to some extent about the body to provide an approximately circular cross-section to the radiation. The material 3 may be water or a viscous or particulate material in one or more flexible bags. The body 1 is retained firmly in a desired position by means such as a retaining strap 4.

The bed 2 and the body 1 are inserted into an opening 5 in a rotatable member 6 so that a selected cross-sectional slice of the body is disposed in the opening. Bed 2 may include supports on either or both sides of the member 6 but has been shown in FIG. 1 to include supports only at the rear for the sake of clarity. The rotatable member 6 is arranged to rotate about an axis 7, longitudinal of the body and perpendicular to the paper. For that purpose, the member 6 is supported and/or guided by three gear wheels 8a, b, c, which engage with gear teeth (not shown) cut into the periphery of member 6. The gear wheels 8 are journalled in a main frame 9 of the apparatus, which may take any form suitable to support the apparatus and to allow the necessary rotation. A further gear wheel 10, also engaging with the said gear teeth is driven by an electric motor 11, also mounted on the main frame 9 and serves to provide the required rotary motion.

The rotatable member 6 also carried a source 12 of a fan-shaped spread 15 of X-rays, a bank of detectors 13 and a bank of associated collimators 14. The detectors, which in a typical embodiment number 120, can be of any suitable type, for example scintillation cyrstals with associated photomultipliers or photodiodes.

The source 12 may be of any known type capable of producing the fan-shaped spread 15 of X-rays and may be of the type in which the point source of the radiation can be scanned across the surface of the anode to change the position of the fan of X-rays. That shown in FIG. 1, however, is fixed in relation to the detectors 13. In this example the source 12 and detectors 13 are substantially equidistant, each about 50cm., from axis 7 although this may be varied if desired provided the geometry of the arrangement is accurately known.

In operation the source 12 irradiates body 1 with the fan 15 of X-rays. The X-rays are partially absorbed by the body and the intensity, after such absorption, is measured by detectors 13. Each detector receives radiation transmitted through the body along a respective one of a group of mutually divergent beam paths. The dimensions of the paths are related to the dimensions of the associated one of collimators 14. The output of each detector is applied to a respective channel, of which only one is shown in the drawing, and each channel comprises, in series, an amplifier such as 16, an integrator such as 17, an analogue-to-digital converter such as 20 and a log converter circuit such as 21. Each integrator integrates the signal in its channel for a period representing a predetermined degree of rotational motion to provide an analogue signal representing the total intensity of radiation incident on the respective detector in that time and transmitted through the body 1 along a path effectively examined by that detector (taking into account the rotational motion). To provide the information regarding the rotation a circular graticule 18 is provided mounted coaxially on the shaft of cog wheel 10. This graticule takes the form of a translucent ring carrying radial engraved lines. The lines can interrupt a light path between a light source and photocell included in a photocell unit 19 mounted on main frame 9. Thus as cog wheel 10 rotates, driving rotary member 6, successive lines interrupt the light path and photocell unit 19 provides pulses at a repetition rate indicative of the rate of the rotary motion. The pulses are provided to integrators 17 for setting and resetting at the desired intervals thus providing the said analogue signals. Output conductors such as 22 convey the signals in all the channels to a processing circuit (not shown in FIG. 1) which operates on the signals to evaluate the absorption coefficient, with respect to the radiation from source 12, at each of a plurality of locations distributed over the examined region of the body 1.

It will be apparent that all path lengths of the radiation through body 1 are not equal, in view of the approximately circular cross-section of the body and surrounding material. For this reason the outer detectors of the array tend to give higher outputs than centrally disposed detectors, even for a body of uniform absorption. This may be mitigated, for example, by providing suitably shaped attenuating bodies between source 12 and body 1 and/or between body 1 and detectors 13 to substantially equalise the path lengths. Alternatively, the gains of the respective detectors and/or amplifiers may be appropriately adjusted. Alternatively, or in addition, correction factors may be measured in the presence of an artificial body of uniform absorption such as water in a suitably shaped box or a body phantom of plastic material. Such correction factors may later be subtracted from all readings for the real body 1.

Each output signal provided by a detector relates to the absorption suffered by the radiation from source 12 on traversing a respective beam path through the body 1. It will be appreciated that the output signals derived from the various integrators, such as 17, in response to a given timing pulse relate to a group of mutually divergent beam paths, and that signals relating to further groups of divergent beam paths will be derived in response to successive timing pulses. The relationship between the giming pulses and the angular separation of adjacent beam paths is such that, if there are $n$ detectors, then $(n-1)$ of them will provide, in response to one timing pulse, output signals which relate to beam paths parallel to beam paths in respect of which other detectors provided output signals in response to the previous timing pulse. Thus, in the course of rotation of the member 6 through a substantial angle, sets of output signals relating to sets of parallel beam paths can be built up. Some of these parallel sets will clearly be completed before others, for example a set of output signals relating to beam paths parallel to the left hand extremity of the spread 15 will have been completed as soon as the member 6 has rotated clockwise through an angle equal to the angle of the fan shaped spread 15 (e.g. 40°). However some of the sets, notably those parallel to beams intermediate the extremes of the spread 15, in the position shown in the drawing, will not be completed until the member 6 has rotated through more than 180°. If signals relating to these sets are required, then the rotation has to be continued at least until it reaches the angle (180° + [fan angle] − [inter-beam angle]). When this is done, however, some redundancy of information occurs, i.e. duplicated signals are obtained in respect of some beam paths. Where this occurs, the duplicated signals may be averaged or, alternatively, one of the two signals obtained for a given beam path can be rejected.

The principle of this invention is to maintain the timing pulses at a constant phase in relation to the rotation of member 6 whilst the member 6 moves through a first substantial angle, thus causing each detector to provide, in sequence, output signals relating to beam paths in different parallel sets, and then, at a suitable stage in the rotational movement, to shift the phase of the timing pulses relative to the rotation of member 6 so as to cause each detector, during further movement of said member through another substantial angle, to provide output signals relating to beam paths in parallel sets interleaved in angle with the first mentioned parallel sets.

In accordance with a feature of the invention, the aforementioned matters of completeness of output signals relating to certain parallel sets of beam paths and of redundancy of information are both taken account of by means of a form of strobing technique, employed at the phase-shifting stage, to arrange that the shift is not applied simultaneously to the timing pulses for all detectors. Instead, the phase shift is applied to the timing pulses for each detector just prior to the stage at which that particular detector would have commenced to supply redundant information. By this means output signals relating to complete sets of both and interleaved beam paths are obtained in a total rotation of (360° − [inter-beam angle]).

It is convenient, for the sake of simplicity, to consider that there are only five beams of radiation having their centre lines distributed equi-angularly (i.e. at 10° spacing) across the spread 15 of radiation. In this case, of course, only five detectors $13_1$ to $13_5$ are included in the bank 13 and correspondingly only five sets of the circuits 16, 17, 20 and 21 are required.

In FIG. 2, the five sets of circuits 17, 20 and 21 are shown, each set bearing a suffix which is characteristic of the detector to which it is connected; the suffices 1 and 5 relating to the detectors for the outermost beams at the left and right-hand sides respectively of the spread (in the position shown in FIG. 1), suffix 3 relating to the detector for the central beam, which always passes through the axis of rotation, and suffices 2 and 4 relating to the detectors for the intermediate beams at the left and right-hand sides respectively of the central beam.

As shown in FIG. 2, each integrator 17 receives the timing pulses from the unit 19 via a respective switch 23, the switches 23 being shown as single pole, two-way mechanical switches although it will be appreciated that in practice they are transistor or diode switches. The timing pulses from unit 19 take the form shown at 24, consisting of spike-like pulses, such as 25 and 26, which effect the reading and resetting of the integrators 17, successive pulses being separated by a time T. These pulses are applied directly to one switched contact of each of the switches 23 and also, via a delay element 27, to the other switched contact of each of the switches. The poles of all the switches 23 are directly connected to their respective integrators. The delay element 27 is arranged to impart, to the pulses applied thereto, a delay equivalent to one half of the time T.

The undelayed timing pulses are also applied to a master timing circuit 28 which controls the operation of the switches 23 as well as some other components which will now be described.

The signals appearing at the outputs 22 of all five channels are applied to a sorting circuit 29 which sorts the output signals into sets relating to substantially parallel beam paths through the body 1. For reasons of geometry, the signals so selected do not relate to uniformly spaced parallel beam paths, and since the preferred technique for processing the output signals to evaluate said coefficients (the technique described and claimed in U.S. Pat. No. 3,924,129 requires that, for high accuracy of operation, signals be presented in sets relating to uniformly spaced, parallel beam paths, a suitable equalising circuit 30 is provided to compensate for said non-uniformity of spacing. The circuit 30 can be, for example, a suitable interpolating circuit arranged to accept the sorted signals and provide new signals which relate to uniformly spaced beam paths, though it will be appreciated that some at least of the new signals will have been synthesised from suitably combining appropriate proportions of two or more of the real output signals.

Circuit 30 feeds a convolving circuit 31 of the kind described and claimed in the aforementioned U.S. Pat. No. 3,924,129 in which the absorption coefficients are evaluated, and the coefficients so evaluated are applied, by way of a window height and width control circuit 32 of known kind to a visual display unit 33. The unit 33 conveniently comprises a cathode ray tube with facilities for photographing the picture displayed thereon. The evaluated coefficients are also conveyed from circuit 31 to a long term store 34 which may comprise magnetic tape or disc storage means. The operations of units 29, 30 and 31 at least are controlled under the influence of the master timing circuit 28.

The operation of the apparatus in accordance with this example of the invention will now be described with reference to the drawings and to the table which shows how sets of output signals relating to parallel beam paths are built up as the member 6 rotates around the body. For the purposes of the following description, it is convenient to assume that the various beam paths are obtained at unique angular positions of the member 6, rather than over a finite time during which the member rotates, as is the case in practice. It will be assumed that sets of output signals are obtained each time the member 6 has rotated through 10°, the inter-beam angle.

Referring now to the table, the rows indicate the successive angular positions of member 6 relative to the starting position shown in FIG. 1 and the columns indicate the angle of a beam relative to the extreme right-hand beam of the spread in said starting position. The numbers 1 through 5 entered at respective row/column intersections indicate the detector 13 which is for the time being providing an output signal indicative of the beam path through the body characterised by the ordinate and abscissa values concerned.

Thus, as the member 6 is rotated in a clockwise direction, it will be appreciated that the complete parallel set of five beams at 40° to said extreme right-hand beam has been built up after only 40° of rotation of the member 6; this being signified by the complete sequence of numbers 1 through 5 listed in the relevant column. The sets at 0°, 10°, 20° and 30° remain incomplete at this stage, as indicated by the incomplete columns of figures under the respective headings. Further rotation of member 6 causes further complete sets of output signals to be built up in sequence, as can be seen from the table, and this procedure continues unchanged until the member 6 has rotated through 140°. At this stage, if the timing pulses applied to the integrator 17, remained of the same phase, the detector $13_1$ (which feeds integrator $17_1$) would provide an output signal relating to the same beam path for which the detector $13_5$ (which feeds integrator $17_5$) produced an output signal when the member 6 was in its initial (0°) position. This is a characteristic of the geometry of the apparatus and, with the notation used in the Table, duplicated beam paths are characterised by the two detector suffices concerned adding up to six. This only applies, of course, to beam paths irradiated at angular positions of member 6 spaced apart in absolute terms by more than the fan angle. In order to avoid duplication of output signals relating to the first group of sets of beam paths (i.e. those occurring at 0°, 10°, 20° etc.) the timing circuit 28 is arranged to actuate switch 23, so as to apply the delayed timing pulses to integrator 17, thus causing the relevant detector $13_1$ to provide an output signal indicative of a beam path angled at 175° to said extreme right-hand beam of the spread and commences the derivation of signals from a second group of sets of beam paths exactly interleaved with the paths of the first group of sets. The remainder of the detectors, however, are all still occupied in providing information relating to the first group of sets.

The next integrator to suffer a change in the phase of the timing pulses applied thereto is $17_2$. This occurs when the member 6 has rotated through 160° and avoids the duplication of the output signal which would otherwise have been obtained from the relevant detector $13_2$ with that obtained for the 10° set at the initial 0° position from the detector $13_4$ which feeds integrator $17_4$.

The process of changing the phase of the timing pulses applied to the various integrators at appropriate times continues until all of the integrators are being supplied with the delayed timing pulses. This condition then remains unchanged to the end of the rotational movement of member 6, which in this example is 350°. The switches 23 can be set to their starting positions (i.e. connecting the undelayed timing pulses to the integrators) either by a mechanical resetting device or by a signal from timing circuit 28 as the member 6 completes its rotation and assumes its starting (0°) position. By this means, output signals relating to the entire second group of sets are provided; the second group of sets being interleaved in angle with the first group.

It will be appreciated that for the purpose of controlling the switches 23 the timing circuit 28 can include a ring counter which accumulates a count in response to the receipt of the timing pulses from unit 19 and provides output signals on respective terminals when the accumulated count reaches selected amounts. The switching procedure is, of course, predetermined by the geometry of the apparatus and is the same for all examinations.

If desired, the apparatus can be operated without the interleaving facility and the rotation merely performed through 210° (i.e. 180° + [fan angle 40°] − [inter-beam angle 10°]). In this case the appropriate outputs from the timing circuit 28 can be used to reject the duplicated output signals which would be derived from the detectors $13_1$ to $13_4$ feeding integrators $17_1$ to $17_4$ over the rotational period from 140° to 210°.

The invention can also be applied with advantage to apparatus of the kind described in U.S. applications Ser. Nos. 630,779 and 733,941 in which the X-ray source 12 is such that the electron beam can be scanned over an elongated anode so as to effectively shift the spread 15 in relation to the body. The scanning of the electron beams is, of course, synchronous with the rotation of the member 6.

In operation, therefore, assuming that five detectors are spread over the 40° fan of radiation, so that the interbeam angle (i.e. the angle between the centre-lines of adjacent beams of radiation) is 10°, the integrators 17 will provide output signals relating to a group of five mutually divergent beam paths through the body in response to the receipt of each timing pulse, such as 25, 26. The timing pulses will be produced at a rate of one per 10° rotation of the turntable 6 and clearly the graticule and the photocell arrangement 18, 19 are constructed to achieve this. Such arrangements are well known for monitoring not only rotational but also linear movement of a member. A photocell and graticule arrangement functioning as a linear motion transducer is illustrated in the book "Analog-Digital Conversion Techniques", edited by Alfred K. Susskind and published in 1957 jointly by the Technology Press of the Massachusetts Institute of Technology and John Wiley & Sons, Inc., at pages 6-31 and 6-32 with reference to FIGS. 6–14 thereof.

Returning to the scanning procedure, it will be evident from the foregoing that if the turntable 6 were allowed to rotate to the 140° position with no change in the phase of the timing pulses applied to the integrator $17_1$, that integrator would start to produce duplicated information. Thus once the integrator $17_1$ has provided the signal for the beam at 170°, the appropriate switch $23_1$ is actuated by the timing circuit 28 to cause the delayed timing pulses from element 27 to be applied to integrator $17_1$. This integrator then produces signals relating to beams at 175°, 5°, 15° etc. which are interleaved with the beams for which that detector has previously provided output signals. Likewise, the switch $23_2$ is changed after the integrator $17_2$ has provided a signal relating to a beam at 0° (after 150° rotation of the turntable) and this process continues with the timing pulses fed to integrator $17_3$ being changed in phase after 170° rotation of turntable 6 and so-on. Clearly the phase of the timing pulses fed to all integrators will have been changed by the time that the turntable has rotated through 220° and from that time until the turntable has rotated through 350° all of the integrators are fed with the delayed timing pulses and are thus providing output signals indicative of beams interleaved in angle with those in respect of which output signals were provided in response to the undelayed timing pulses.

The effect is, therefore, that by using the invention it is possible to obtain during 350° of rotation, and using five detectors, substantially the same information as could have been obtained during 210° of rotation and using ten detectors if the invention were not used.

What we claim is:

1. Radiographic apparatus comprising a source of a substantially planar spread of penetrating radiation, means for supporting said source to project said radiation across an opening in which a body to be examined can be inserted, the spread of radiation being disposed to irradiate a selected cross-sectional slice of said body, means for angularly moving said means for supporting, and with it said source, about an axis intersecting said slice, a plurality of detector devices disposed to receive radiation directed through said slice along a plurality of groups of divergent beam paths, in said slice, during said angular movement, a signal channel for each detector device arranged to receive output signals, developed by said detector devices and indicative of the absorption suffered by said radiation on traversing said beam paths, and means for generating timing signals for application to said channels to distinguish the output signals relating to each of said groups, said timing signals being related to the angular movement of said means for supporting relative to said body, and means, effective during said angular movement for changing the relationship between said timing signals and said angular movement, so as to derive output signals relating to more of said groups of beam paths than would have been available without said change of relationship.

2. Apparatus according to claim 1 wherein said means for changing the relationship between said timing signals and said angular movement includes selectively operable switch means associated with each of said channels.

3. Apparatus according to claim 2 including means for operating said switch means in a predetermined sequence so as to change said relationship at different times in different channels.

4. Apparatus according to claim 3 wherein said means for operating said switch means changes said relationship for each channel immediately prior to the time when, if said relationship had not been changed, that channel would have commenced producing duplicated information with progress of said angular movement.

5. Apparatus according to claim 2 wherein each said switch means comprises a transistor switch device having an input terminal connected to receive control signals.

6. Apparatus according to claim 5 including a timing control circuit adapted to receive said timing signals and to utilise said timing signals to generate said control signals.

7. Apparatus according to claim 6 wherein said timing control circuit includes a counting circuit which counts said timing signals and generates said control signals in response to the count assuming selected valves.

8. Apparatus according to claim 2 wherein each channel includes a resettable integrator circuit and said timing pulses are applied to said integrator circuits to act as reading and re-setting signals therefor.

9. Apparatus according to claim 1 including a delay component connected to receive said timing pulses and to supply delayed timing pulses to said channels, means for applying said delayed timing pulses and the undelayed timing pulses to each switch means, and wherein each switch means is adapted to supply either said delayed or said undelayed timing pulses to its respective channel.

* * * * *

UNITED STATES PATENT AND TRADEMARK OFFICE
CERTIFICATE OF CORRECTION

PATENT NO. : 4,091,286
DATED : May 23, 1978
INVENTOR(S) : ALLAN BEATTIE LOGAN, ROBIN GEOFFREY MARSH and
IAN ALEXANDER FLEMING It is certified that error appears in the above-identified patent and that said Letters Patent are hereby corrected as shown below:

Column 2, line 28, delete "onlly" and insert -- only --.

Column 3, line 3, delete "cyrstals" and insert -- crystals --.

Column 4, line 12, delete "giming" and insert -- timing --.

Column 10, line 3 (Claim 9), delete "1" and insert -- 2 --.

Signed and Sealed this

Sixth Day of March 1979

[SEAL]

Attest:

RUTH C. MASON
Attesting Officer

DONALD W. BANNER
Commissioner of Patents and Trademarks